US009876470B2

(12) United States Patent
Biel et al.

(10) Patent No.: US 9,876,470 B2
(45) Date of Patent: Jan. 23, 2018

(54) MEDICAL AMPLIFIER ISOLATION

(71) Applicant: CARDIOINSIGHT TECHNOLOGIES, INC., Cleveland, OH (US)

(72) Inventors: Arkadiusz Biel, Toronto (CA); Harold Wodlinger, Thornhill (CA); Richard M. Fine, Mississauga (CA)

(73) Assignee: Cardioinsight Technologies, Inc., Cleveland, OH (US)

( * ) Notice: Subject to any disclaimer, the term of this patent is extended or adjusted under 35 U.S.C. 154(b) by 118 days.

(21) Appl. No.: 14/434,922

(22) PCT Filed: Oct. 11, 2013

(86) PCT No.: PCT/US2013/064595
§ 371 (c)(1),
(2) Date: Apr. 10, 2015

(87) PCT Pub. No.: WO2014/059308
PCT Pub. Date: Apr. 17, 2014

(65) Prior Publication Data
US 2015/0263673 A1    Sep. 17, 2015

Related U.S. Application Data

(60) Provisional application No. 61/713,022, filed on Oct. 12, 2012.

(51) Int. Cl.
*H03F 1/02* (2006.01)
*H03F 3/45* (2006.01)
(Continued)

(52) U.S. Cl.
CPC ............... *H03F 1/02* (2013.01); *A61B 5/04* (2013.01); *A61B 5/04004* (2013.01); *A61B 5/0408* (2013.01); *A61B 5/0476* (2013.01); *A61B 5/04082* (2013.01); *H03F 3/45076* (2013.01); *A61B 2562/182* (2013.01); *H03F 2200/372* (2013.01); *H03F 2203/45151* (2013.01)

(58) Field of Classification Search
USPC .................................................. 330/252–261
See application file for complete search history.

(56) References Cited

U.S. PATENT DOCUMENTS

| 5,392,784 A | 2/1995 | Gudaitis |
| 2003/0013965 A1 | 1/2003 | Quistgaard et al. |

(Continued)

OTHER PUBLICATIONS

Int'l Search Report—3 pgs., dated Jul. 28, 2014, CardioInsight Technologies, Inc.

(Continued)

*Primary Examiner* — Hieu Nguyen
(74) *Attorney, Agent, or Firm* — Tarolli, Sundheim, Covell & Tummino LLP

(57) ABSTRACT

This disclosure provides isolation for a medical amplifier by providing a low impedance path for noise across an isolation barrier. The low impedance path can include a capacitive coupling between a patient ground, which is isolated from control circuitry, and a functional ground of an isolation system that is isolated from earth ground. The low impedance path can draw noise current from an input of an amplifier of patient circuitry.

23 Claims, 3 Drawing Sheets

(51) Int. Cl.
    *A61B 5/0408*    (2006.01)
    *A61B 5/0476*    (2006.01)
    *A61B 5/04*      (2006.01)

(56) References Cited

U.S. PATENT DOCUMENTS

| | | |
|---|---|---|
| 2004/0056103 A1* | 3/2004 | Sepponen .......... A61B 5/04282 |
| | | 235/487 |
| 2008/0146894 A1 | 6/2008 | Bulkes et al. |
| 2009/0018429 A1 | 1/2009 | Saliga et al. |
| 2010/0301215 A1 | 12/2010 | Gonopolskiy et al. |

OTHER PUBLICATIONS

Written Opinion—8 pgs., dated Jul. 28, 2014, CardioInsight Technologies, Inc.

* cited by examiner

MEDICAL AMPLIFIER ISOLATION

CROSS-REFERENCE TO RELATED APPLICATION

This application is a 371 of PCT/US2013/064595, filed Oct. 11, 2013 and entitled MEDICAL AMPLIFIER ISOLATION, which claims priority to U.S. Provisional Application No. 61/713,022, filed Oct. 12, 2012 and entitled MEDICAL AMPLIFIER ISOLATION. Each of the above-identified applications is incorporated herein by reference in their entirety.

TECHNICAL FIELD

This disclosure relates to medical amplifier isolation systems and method.

BACKGROUND

Medical amplifiers can be implemented for a variety of devices used in connection with patient treatment procedures and/or medical diagnoses. Medical amplifiers can be configured in a manner to isolate a patient from any possible contact with a power source, such as including line voltage and earth ground. Isolation can be implemented in a variety of ways, such as magnetic or optical isolation, to pass signals between a control system and portions of the device that might contact the patient. Some types of isolation can result in the medical amplifier being more susceptible to radiated noise, such as line frequency noise, based on the patient ground not being coupled with earth ground. In these situations, a substantially large common-mode voltage with respect to earth ground can be generated, such that the common-mode voltage generates a current flow from the patient to earth ground via a parasitic capacitance, thus generating a differential voltage that cannot be rejected by the medical amplifier.

SUMMARY

This disclosure relates to isolation for a medical amplifier system.

As an example, a medical amplifier system includes a patient circuitry stage configured to receive electric signals from the patient and provide corresponding output signals. The patient circuitry stage can include an electrical connection to a patient ground. The system also includes control circuitry configured to process the corresponding output signals. An isolation system can be configured to electrically isolate the patient circuitry stage and the control circuitry by including a functional ground that is capacitively coupled to the patient ground but electrically isolated from the control circuitry.

As another example, an apparatus can include an isolation system configured to be connected between and provide electrical isolation between patient-side circuitry and other circuitry. The isolation system can include a patient isolation stage comprising at least one signal input configured to connect to a signal path of the patient-side circuitry and a power input configured to connect to a power path of the patient circuitry. At least one other isolation stage can be connected between the patient isolation stage and the other circuitry. Such other isolation stage can include a corresponding signal path configured to communicate signals from the signal path of the patient-side circuitry signal to the other circuitry and a separate power path configured to provide input power from the other circuitry to the power path of the patient isolation stage. A capacitive coupling is connected across the patient isolation stage between a patient ground of the patient-side circuitry and a functional ground of the isolation system, the other isolation stage being configured to electrically isolate the functional ground from the other circuitry.

DETAILED DESCRIPTION

This disclosure relates to medical amplifier isolation systems and related methods. As an example, a medical amplifier system can include an isolation system that includes multiple stages of isolation between patient circuitry, including an amplifier, and non-isolated control and processing circuitry. A capacitance can be provided across a patient-side isolation barrier, such as by capacitively coupling a patient ground and an isolated functional ground. The capacitance between such grounds can establish a lower impedance path for noise current than parasitic capacitors to earth ground in the amplifier system. The medical amplifier thus can substantially reduce the magnitude of current flowing between the patient and earth ground via a parasitic capacitance, resulting in an increased signal to noise ratio, while also being capable of meeting or exceeding standard requirements for isolation and leakage current.

Figure 1:
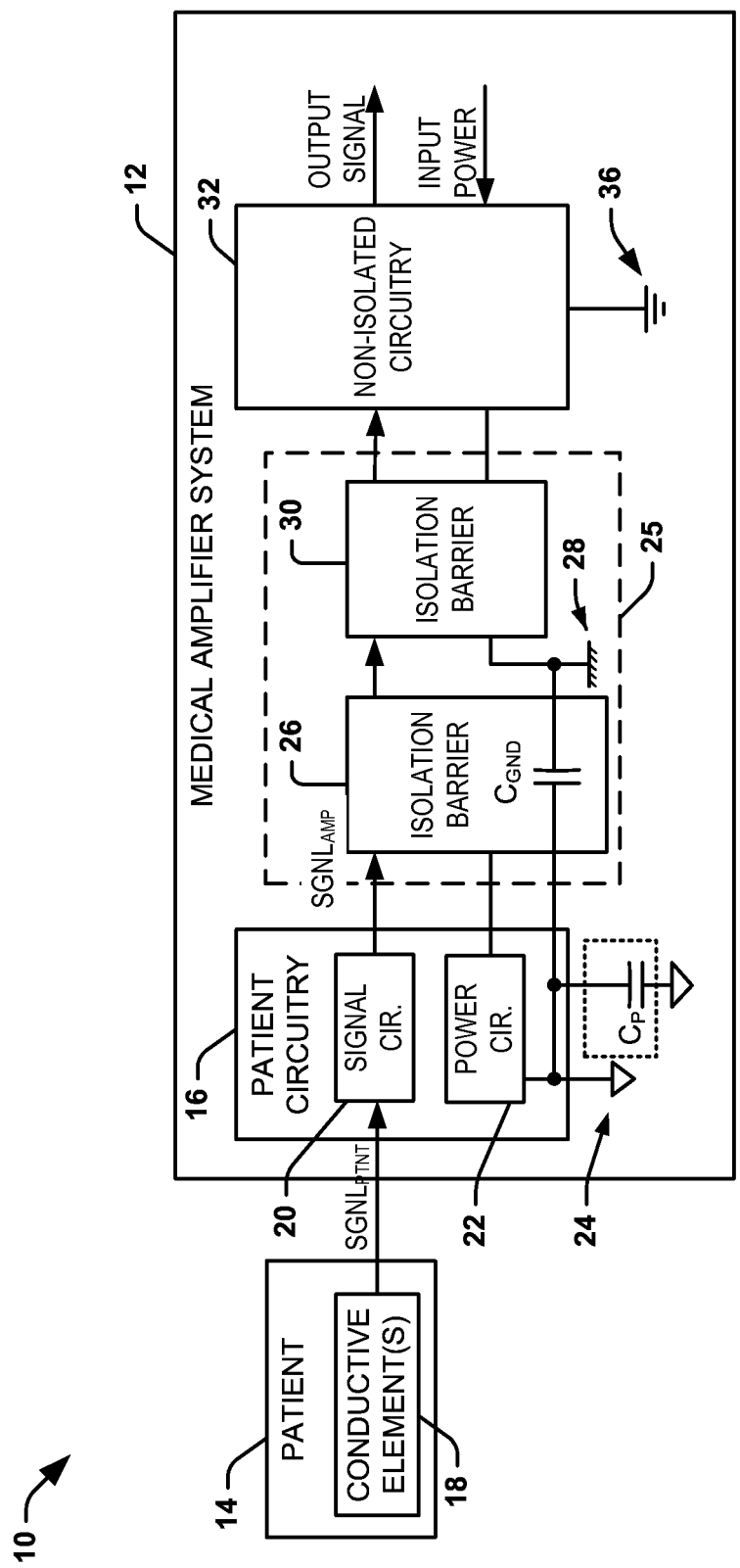
FIG. 1 depicts an example of a medical amplifier system implementing an isolation system.

FIG. 1 depicts an example of a system 10 that includes medical amplifier system 12. The medical amplifier system 12 can be implemented in a variety of medical applications for administering treatment to or obtaining diagnostic information from a patient 14, for example. The medical amplifier system 12 includes a patient circuitry stage 16 that can be coupled to the patient 14 via electrically conductive leads terminating to sensor elements 18, such as electrodes or probes. The sensor elements can be passive sensor electrodes or active circuit components can also be implemented at the electrodes.

The patient circuitry stage 16 can thus receive signals $SGNL_{PTNT}$ from the patient 14 via the sensor elements 18. There can be any number of sensor elements 18, and the patient circuitry 16 can include circuitry for processing signals provided by each such conductors. The sensor elements 18 can be non-invasive (e.g., positioned on the surface of the patient's body) and/or be invasive (e.g., percutaneously or otherwise positioned within the patient's body).

In the schematic example of FIG. 1, the patient circuitry stage 16 includes signal circuitry 20 and power circuitry 22. The patient circuitry 16, including the signal circuitry 20 and power circuitry 22, can operate electrically relative to a patient ground 24. The power circuitry 22 can be configured to deliver electrical power (e.g., regulated DC power) to the patient circuitry 16, including the signal circuitry 20. While for purposes of ease of explanation the signal circuitry 20 and the power circuitry 22 are demonstrated as separate blocks, it is to be understood that power and processing circuitry can be structurally integrated together in other examples.

The signal circuitry 20 can include one or more amplifiers that can be configured to amplify each of the patient signals $SGNL_{PTNT}$, such as anatomically generated electrical impulses. The signal circuitry 20 can be configured to amplify the signals $SGNL_{PTNT}$ and provide corresponding amplified signals $SGNL_{AMP}$ to one or more corresponding non-isolated circuitry 32. The non-isolated circuitry 32 can operate electrically relative to an earth ground that is electrically isolated from the patient ground 24. Specifically, the amplifier system 12 includes an isolation system 25 configured to electrically isolate the patient circuitry from the non-isolated circuitry 32.

As a further example, the signal circuitry 20 can be configured (e.g., by including an analog-to-digital converter) to provide the amplified signals $SGNL_{AMP}$ as digital signals. As an example, the non-isolated circuitry 32 can include processing circuitry, such as to implement signal conditioning and filtering on the amplified signals $SGNL_{AMP}$ provided by the isolated patient circuitry 16. The non-isolated circuitry 32 can in turn provide processed version of the amplified signals $SGNL_{AMP}$ for subsequent processing (e.g., by an EC mapping hardware and software and/or other diagnostic equipment) via the signal path.

In other examples, the non-isolated circuitry 32 can generate control signals to the patient circuitry stage 16 and/or the patient 14. For example, the control signals can be utilized to configure the patient circuitry stage 16, including the signal circuitry 20. As another example, the control signals may be used to control delivery of therapy to the patient 14 across the isolation system 25. Control signals can also be generated by the patient circuitry 16 and provided to the non-isolated circuitry 32 via the signal path through the isolation system 25.

The isolation system 25 is configured to electrically isolate the patient circuitry 16 from the non-isolated circuitry 32. The isolation system 25 can include more than one isolation barrier 26 and 30. Each isolation barrier 26, 30 can be configured to provide one type of isolation for data/information signals (e.g., optical isolation) and another type of electrical isolation (e.g., magnetic isolation) for power signals that are being provided between the patient circuitry and the non-isolated circuitry 32. Other types of isolation can be implemented for communication of data and power between the patient circuitry and the non-isolated circuitry.

In the example of FIG. 1, the non-isolated circuitry 32 can be coupled to receive input power from a power source (not shown—e.g., approximately 120 VAC/60 Hz or 230 VAC/50 Hz or regulated DC power). For instance, the non-isolated circuitry 32 can be connected between a line voltage and earth ground 36. The isolation system 25 thus is configured to provide electrical isolation between the patient 14 and the power source, such that a patient ground 24 is not electrically coupled with earth ground 36 to which the circuitry 32 is connected. The data and information signals (e.g., including the signals $SGNL_{AMP}$) and power can thus be communicated across the isolation system 25 between the non-isolated circuitry 32 and the patient circuitry 16. In the example of FIG. 1, while the non-isolated circuitry 32 is demonstrated as coupled to earth ground 36, it is to be understood that the low-voltage rail reference could be a variety of low-voltage amplitudes electrically isolated from patient ground 24, and is not limited to earth ground.

In some circumstances, the isolation system 25 can render the medical amplifier system 12 more susceptible to radiated noise, such as line frequency noise or other noise that exists within the bandwidth being measured. This susceptibility is based on the isolation of the patient ground 24 with respect to earth ground 36. Isolating the patient 14 can result in the patient ground voltage potential to "float", such as based on electric fields acting upon the patient 14, and thus inducing a leakage current to flow from the patient ground 24 to earth ground 36 via a parasitic capacitance $C_P$. The parasitic capacitance $C_P$ is distributed around the device and the cabling, so currents through any part of the device will vary. As a result, the patient circuitry stage 16 can generate a substantially large common-mode voltage with respect to earth ground 36. The common-mode voltage can generate a common-mode current that can induce a differential voltage in the amplified signals $SGNL_{AMP}$ that cannot be rejected by the medical amplifier system 12. For example, the common-mode current flow can instantiate a differential voltage with respect to input resistors associated with the signal circuitry 20, which can be transmitted as noise in the signals $SGNL_{AMP}$. The amount of current flow leakage may be reduced by employing matched resistors, but this alone still tends to be insufficient for achieving high common mode rejection (e.g., greater than −100 dB, such as about −140 dB or more).

To substantially mitigate the common-mode current flow, the medical amplifier system 12 includes a capacitive coupling $C_{GND}$ connected across the patient isolation system 25 between the patient ground 24 and a functional ground 28 residing between separate isolation stages in the isolation system. For example, the capacitive coupling $C_{GND}$ can be configured as one or more physical capacitors having a capacitance that is greater than the parasitic capacitance $C_P$. As a result, the capacitive coupling $C_{GND}$ can provide a lower impedance path across the isolation system 25. The low impedance path effectively causes the functional isolation stage to float at approximately the same voltage as the patient isolation stage. Such a low-impedance path substantially reduces a voltage difference across the parasitic capacitance $C_P$. As a result, a substantially large portion of the leakage current that can cause the common-mode current can flow through the capacitive coupling $C_{GND}$ instead of the parasitic capacitance $C_P$, resulting in significantly reduced leakage current and correspondingly reduced differential voltage at the input of the signal circuitry 20. As a further result, the sensed signals at the input of the amplifier exhibit an improved common mode rejection ratio (e.g., by about 20 dB or more).

Additionally, the total amount of leakage current in the system 10 is about the same as a system having a single isolation barrier. This is because the magnitude of the leakage current is determined by the size of the parasitic capacitors at the patient stage, and across the final isolation barrier to earth ground. Since the size of the parasitic capacitors does not change when a functional isolation stage is added, such as disclosed herein, patient safety is not compromised.

Figure 2:
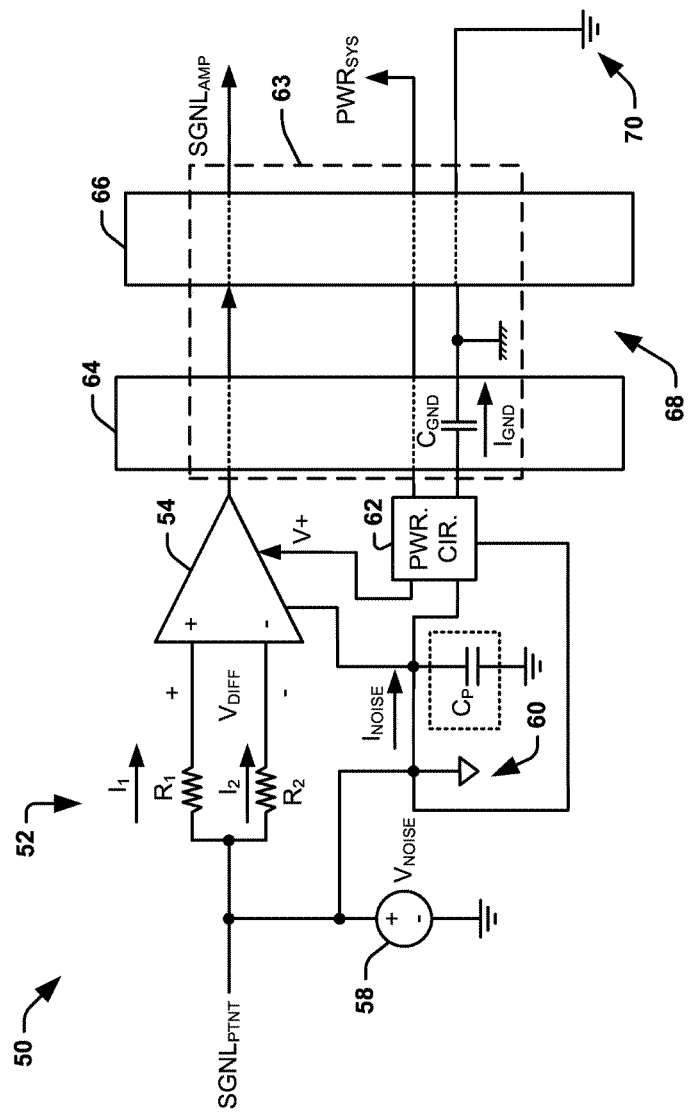
FIG. 2 depicts an example diagram of medical amplifier system that can be implemented.

FIG. 2 depicts a schematic diagram of an example of a medical amplifier system 50 that can be implemented. The amplifier system 50 includes a patient-side circuitry stage 52, such as can correspond to the patient circuitry stage 16 of the medical amplifier system 12 in the example of FIG. 1. Therefore, reference can be made to FIG. 1 in the following description of the example of FIG. 2.

The patient circuitry stage 52 includes an amplifier 54 that is configured to generate an amplified signal $SGNL_{AMP}$ in response to a patient input signals $SGNL_{PTNT}$. The patient signals $SGNL_{PTNT}$ can correspond to one or more electrical signals measured from the patient, such as via conductive elements (e.g., sensor electrodes) that are coupled to the patient. In some examples, the conductive elements can be electrodes distributed across a patient's torso, such as noninvasively covering the entire torso or a predetermined portion thereof. For instance, the electrodes can be arranged on the patient's torso, such as for acquiring electrical signals for electrocardiographic mapping or for gathering electrocardiograph (ECG) or electroencephalograph (EEG) diagnostics. Additionally, each electrode can define a respective input channel that provides a corresponding patient signal $SGNL_{PTNT}$ to a respective amplifier 54, each of which amplifiers can be electrically isolated based on the teachings herein. The amplifier 54 as well as other patient-side circuitry 52 can be powered by patient-side power circuitry 62 that is supplied power via a power path of an isolation system 63 such as disclosed herein. The power circuitry 62 thus can establish a high voltage rail (e.g., a regulated voltage) demonstrated as V+ that is relative to a low voltage rail corresponding to patient ground 60. The power circuitry 62 can similarly also, for example, establish a negative voltage rail V− (not shown) relative to the patient ground 60.

In the simplified example of FIG. 2, the amplifier 54 can include a first input resistor $R_1$ coupled to a non-inverting input and a second input resistor $R_2$ coupled to an inverting input. The amplifier 54 thus provides an amplified output signal $SGNL_{AMP}$ to signal processing and control circuitry (not shown, but see, e.g., circuitry 32 of FIG. 1) through two or more isolation stages, demonstrated at 64 and 66. Each isolation stage 64, 66 can be configured to communicate power and data in a manner that affords electrical isolation between the input and output thereof. Since the manner of electrical isolation being implemented can vary according to design considerations and application requirements, the isolation for data and power are demonstrated as dotted lines extending across the blocks corresponding to the isolation barriers 64 and 66. As mentioned above, for example, optical isolation can be utilized for communicating data, such as by employing digital optical communication of the amplified output signal $SGNL_{AMP}$. Magnetic or inductive electrical isolation (e.g., via a transformer) can be employed to communicate the power across each isolation barrier 64 and 66, for example.

In the example of FIG. 2, the medical amplifier system 50 is demonstrated as including a voltage source 58 to represent a noise voltage $V_{NOISE}$ that can be applied onto the patient signals $SGNL_{PTNT}$. In the absence of an isolation system implemented based on the teachings herein, the voltage $V_{NOISE}$ induces a current to flow through each of the input resistors $R_1$ and $R_2$, demonstrated in the example of FIG. 2 as currents $I_1$ and $I_2$, respectively. These currents will vary since the parasitic capacitance differs across the different parts of the circuits. The magnitudes of the induced currents $I_1$ and $I_2$ can also vary relative to each other based on variations in the internal components of the amplifier 54, as well as the resistances of the resistors $R_1$ and $R_2$, thus exhibiting a differential voltage $V_{DIFF}$ at the input of the amplifier 54. The differential voltage $V_{DIFF}$ can thus be propagated in the output signals $SGNL_{AMP}$ as noise, which, if left uninhibited, can cross the isolation barrier and reduce the performance of the associated medical amplifier system.

By implementing isolation in the manner disclosed herein, the patient ground 60 is caused to "float", which is represented herein by the noise voltage $V_{NOISE}$ and a corresponding current $I_{NOISE}$ that flows from the patient ground 60 to earth ground 70 via a parasitic capacitance $C_P$. The parasitic capacitance $C_P$, for example, can result from a cable coupling the patient circuitry stage 52 to the patient, a metallic casing in which the patient circuitry stage 52 is housed, or a variety of other ways. The parasitic capacitance $C_P$ can be exhibited as a substantially high-impedance current path to conduct a portion of the current $I_{NOISE}$ to flow as a current to earth ground 70.

To mitigate the effects of the noise voltage $V_{NOISE}$, the system 50 includes a shield around the patient circuits (connected to patient ground) and capacitive coupling $C_{GND}$ connected across the isolation barrier 64 between the patient ground 60 to a functional ground 68. The capacitive coupling $C_{GND}$ is configured with a capacitance that is greater than the expected parasitic capacitance $C_P$ ($C_{GND} > C_P$) as to provide a low-impedance current path between the patient ground 60 and the functional ground 68 that resides in functional stage between the respective isolation barriers 64 and 66. Therefore, the capacitive coupling $C_{GND}$ can conduct a much larger portion of the current $I_{NOISE}$ to flow as a current $I_{GND}$ to functional ground 68. The functional ground 68 is electrically isolated from earth ground 70 by the one or more additional isolation barrier 66.

As a result of the inclusion of the capacitive coupling $C_{GND}$ to conduct the current $I_{GND}$ to earth ground 70, the effects of noise at the input of the amplifier 54 based on induced currents $I_1$ and $I_2$ can be significantly reduced. The substantially reduced noise at the input of the amplifier 54 can result in corresponding reduction in the noise that is exhibited in signals $SGNL_{AMP}$. For example, up to about 20 dB improvement in common mode rejection ratio can be expected between a conventional circuit and a circuit employing a capacitive coupling $C_{GND}$ coupled across the isolation barrier 64 between the patient ground and functional ground 68. Accordingly, the associated medical amplifier system 50 (e.g., the medical amplifier system 12) can maintain isolation of the patient from an associated power supply, including earth ground 70, and can achieve superior performance with respect to mitigating noise in the signals $SGNL_{AMP}$ that are received from the patient and sent to across the isolation system to control and processing circuitry.

Figure 3:
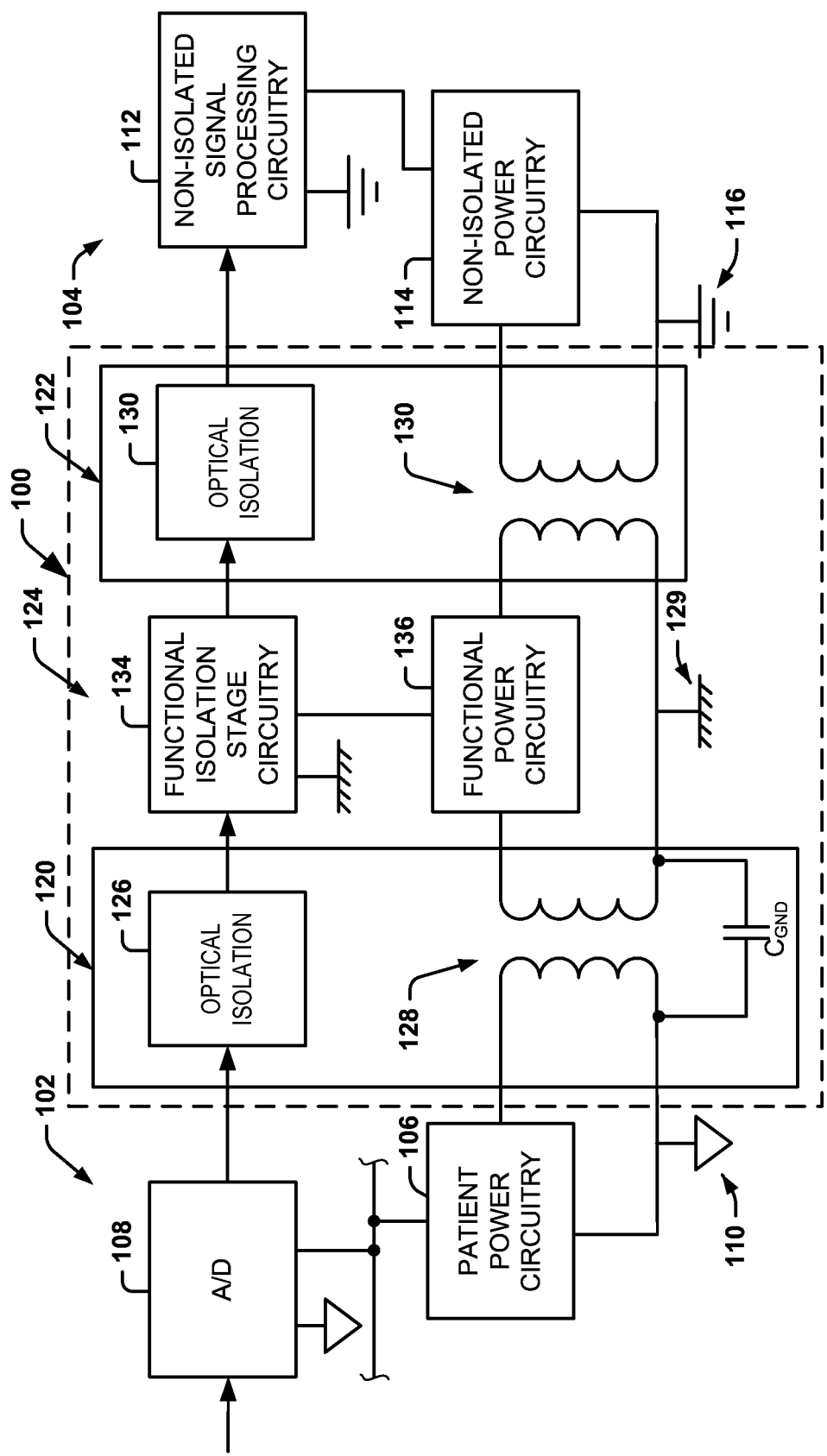
FIG. 3 depicts another example diagram of a medical amplifier system.

FIG. 3 depicts an example of an isolation system 100 such as can be implemented in the medical amplifiers system demonstrated in examples of FIGS. 1 and 2. The isolation system 100 is connected between patient-side circuitry 102 and a non-isolated stage 104. In the example of FIG. 3, the patient-side circuitry 102 can include amplifiers, filters and the like, such as disclosed herein (e.g., FIG. 2). Additionally, as demonstrated in FIG. 3, the patient-side circuitry 102 can include patient power circuitry 106 that is coupled to receive power via the isolation system from an associated non-isolated power circuitry (e.g., a power supply) 114.

The patient power circuitry 106 can drive one or more voltage rails as well as establish a patient ground 110. For example, the patient power circuitry 106 can provide the voltage rail for supplying electrical power to other patient-side circuitry including an analog-to-digital converter, demonstrated at 108. In this way, a digital version of the sensed input signal can be provided as the amplified signal $SGNL_{AMP}$ that is supplied to a signal path of the isolation system 100. The isolation system 100 thus can provide the corresponding digitized output to the non-isolated stage including a non-isolated signal processing circuitry 112. The signal processing circuitry 112 including filtering, digital signal processing and the like is designed to prepare the measured signal. The signal processing circuitry 112 can further include post-processing and visualization of the sensed signals, such as EC mapping or ECG and/or EEG diagnostics, which typically require a high signal-to-noise ratio. The non-isolated power circuitry 114 can be configured to supply power to the non-isolating signal processing circuitry directly and to the patient power circuitry across the isolation barrier as disclosed herein.

As disclosed herein, the isolation system 100 can include a plurality of isolation barriers, demonstrated at 120 and 122. Intermediate the respective isolation barriers 120 and 122 can be a functional stage 124. It is to be understood that the medical amplifier system is not limited to the two isolation barriers 120 and 122, but could include more isolation stages than that disclosed herein. An additional advantage of having two or more isolation stages is that each stage can be designed to withstand a proportional amount the required voltage as mandated by a given medical device standard. For example, where two isolation stages 120 and 122 are provided in a case where it is required to resist 4 KV AC, the components (e.g., transformers and optical isolators) of each isolation stage can be designed to resist about 2 KV AC. Additionally, transformers are more efficient when isolating 2 KV than 4 KV.

The patient-side isolation barrier 120 can include multiple paths for providing electrical isolation for both the signal path and electrical power. For example, optical isolator circuitry can be connected between the A/D converter 108 and the functional stage 124 for providing the signal path through the isolation barrier 120. The optical isolation element (e.g., including an optoisolator or optocoupler) can receive power from the patient power circuitry, for example. The electrical isolation for the power path can be implemented via a transformer 128.

As disclosed herein, the isolation system 100 can include a capacitive coupling $C_{GND}$ connected between the patient ground associated with the transformer 128 and a functional ground 129 that resides in the functional stage 124. The isolation stage 122 can be the same or different from the isolation stage 120 such as including an optical isolation element 130 for the signal path and a transformer 132 for providing electrical isolation along the power path.

In the example of FIG. 3, the functional stage 124 can include additional circuitry and connections for completing the signal path between optical isolation elements 126 and 130 as well as functional power circuitry, including connections 136, connected between the transformers 128 and 132. As an example, the functional isolation stage circuitry 134 can include additional filtering and/or amplifiers configured to perform additional pre-processing for the amplified signals $SGNL_{AMP}$. For example, digital filtering can be performed on the digital signals provided from the optical isolation elements 126. Additionally, filtering and power conditioning can be implemented via the functional power circuitry 136 for improving the power that is provided to the patient power circuitry 106.

While each of the isolation stages 120 and 122 are disclosed as including optical isolation elements and transformers, the types of isolation in the different stages can be the same (as shown) or different. Additionally, different forms of isolation can be provided for information-carrying signals and power from the optical and inductive isolation, such as may include capacitive, giant magnetoresistive, electromagnetic waves, acoustic or mechanical means.

Furthermore, the medical amplifier system has been described as having multi-channel functionality, such that a plurality of patient signals $SGNL_{PTNT}$ and amplified signals $SGNL_{AMP}$ can be communicated across more than one signal channel in the isolation system. Such multichannel implementations can include a single patient ground, a single functional ground and a single earth ground that is shared by the respective channels in each respective isolation stage in the system. As an alternative example, the medical amplifier system could instead implement a separate medical amplifier system for each individual channel, each having its own relative ground connections. Thus, the medical amplifier system can be configured in a variety of ways that can differ from those disclosed herein.

What have been described above are examples. It is, of course, not possible to describe every conceivable combination of components or methodologies, but one of ordinary skill in the art will recognize that many further combinations and permutations are possible. Accordingly, the invention is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A medical amplifier system comprising:
   a patient circuitry stage configured to receive electrical signals from a patient and provide corresponding output electrical signals, the patient circuitry stage comprising an electrical connection to a patient ground;
   at least one control circuitry stage configured to monitor the corresponding output electrical signals provided by the patient circuitry stage; and
   an isolation system electrically isolating the patient circuitry stage from the at least one control circuitry stage, the isolation system comprising a capacitive coupling between the patient ground and a functional ground of the isolation system, the functional ground being electrically isolated from earth ground in the control circuitry stage.

2. The system of claim 1, wherein the isolation system comprises a functional isolation barrier and a patient isolation barrier, the capacitive coupling being connected across the patient isolation barrier, and the functional ground of the isolation system being electrically isolated from the control circuitry stage by the functional isolation barrier.

3. The system of claim 2, wherein the isolation system comprises an isolated functional stage, the isolated functional stage comprising the functional ground and connections configured to pass the signals and power between patient circuitry stage to the control circuitry stage, the isolated functional stage being isolated from the control circuitry stage via the functional isolation barrier and being isolated from the patient circuitry stage via the patient isolation barrier.

4. The system of claim 2, further comprising a functional stage connected between the patient isolation barrier and the functional isolation barrier, the functional stage being electrically isolated from the patient circuitry stage and the control circuitry stage, the functional stage comprising the functional ground and circuitry to process signals provided on the signal path between the patient isolation barrier and the functional isolation barrier.

5. The system of claim 1, wherein the capacitive coupling comprises an isolation capacitor interconnecting the patient ground and the functional ground.

6. The system of claim 1, wherein a capacitance of the capacitive coupling is configured to exceed a parasitic capacitance between the patient ground and earth ground to provide a low impedance path that reduces noise in the patient circuitry stage.

7. A multi-channel amplifier system comprising a plurality of the medical amplifier systems of claim 1, each of the plurality of medical amplifier systems being configured to receive at least one signal from the patient.

8. The system of claim 1, wherein the patient circuitry stage comprises an amplifier configured to amplify each signal received from the patient, the amplifier coupled to the patient ground.

9. The system of claim 1, wherein the patient circuitry stage comprises a differential amplifier configured to amplify the electrical signals received from the patient, the differential amplifier being coupled to the patient ground that is electrically isolated from earth ground by the isolation system, the capacitive coupling providing a low impedance path from an input of the differential amplifier for external noise that is within the bandwidth of the electrical signals being measured.

10. A medical amplifier system comprising:
a patient circuitry stage configured to receive electrical signals from a patient and provide corresponding output electrical signals, the patient circuitry stage comprising an electrical connection to a patient ground;
at least one control circuitry stage configured to monitor the corresponding output electrical signals provided by the patient circuitry stage; and
an isolation system electrically isolating the patient circuitry stage from the at least one control circuitry stage, the isolation system comprising
a functional isolation barrier,
a patient isolation barrier,
an isolated functional stage comprising a functional ground and connections configured to pass the corresponding output electrical signals and power between the patient circuitry stage and the at least one control circuitry stage, the isolated functional stage being isolated from the control circuitry stage via the functional isolation barrier and being isolated from the patient circuitry stage via the patient isolation barrier, and
a capacitive coupling between the patient ground and the functional ground, the capacitive coupling being connected across the patient isolation barrier, the functional ground being electrically isolated from the control circuitry stage by the functional isolation barrier.

11. The system of claim 10, wherein the capacitive coupling comprises an isolation capacitor interconnecting the patient ground and the functional ground.

12. The system of claim 10, wherein a capacitance of the capacitive coupling is configured to exceed a parasitic capacitance between the patient ground and earth ground to provide a low impedance path that reduces noise in the patient circuitry stage.

13. The system of claim 10, wherein the functional ground is electrically isolated from earth ground in the control circuitry stage.

14. A multi-channel amplifier system comprising a plurality of the medical amplifier systems of claim 10, each of the plurality of medical amplifier systems being configured to receive at least one signal from the patient.

15. The system of claim 10, wherein the patient circuitry stage comprises an amplifier configured to amplify each signal received from the patient, the amplifier coupled to the patient ground.

16. The system of claim 10, wherein the patient circuitry stage comprises a differential amplifier configured to amplify the electrical signals received from the patient, the differential amplifier being coupled to the patient ground that is electrically isolated from earth ground by the isolation system, the capacitive coupling providing a low impedance path from an input of the differential amplifier for external noise that is within the bandwidth of the electrical signals being measured.

17. A medical amplifier system comprising:
a patient circuitry stage configured to receive electrical signals from a patient and provide corresponding output electrical signals, the patient circuitry stage comprising an electrical connection to a patient ground;
at least one control circuitry stage configured to monitor the corresponding output electrical signals provided by the patient circuitry stage;
an isolation system electrically isolating the patient circuitry stage from the at least one control circuitry stage, the isolation system comprising
a functional isolation barrier,
a patient isolation barrier, and
a capacitive coupling between the patient ground and a functional ground of the isolation system, the capacitive coupling being connected across the patient isolation barrier, the functional ground being electrically isolated from the control circuitry stage by the functional isolation barrier; and
a functional stage connected between the patient isolation barrier and the functional isolation barrier, the functional stage being electrically isolated from the patient circuitry stage and the control circuitry stage, the functional stage comprising the functional ground and circuitry to process signals provided on a signal path between the patient isolation barrier and the functional isolation barrier.

18. The system of claim 17, wherein the capacitive coupling comprises an isolation capacitor interconnecting the patient ground and the functional ground.

19. The system of claim 17, wherein a capacitance of the capacitive coupling is configured to exceed a parasitic capacitance between the patient ground and earth ground to provide a low impedance path that reduces noise in the patient circuitry stage.

20. The system of claim 17, wherein the functional ground is electrically isolated from earth ground in the control circuitry stage.

21. A multi-channel amplifier system comprising a plurality of the medical amplifier systems of claim 17, each of the plurality of medical amplifier systems being configured to receive at least one signal from the patient.

22. The system of claim 17, wherein the patient circuitry stage comprises an amplifier configured to amplify each signal received from the patient, the amplifier coupled to the patient ground.

23. The system of claim 17, wherein the patient circuitry stage comprises a differential amplifier configured to amplify the electrical signals received from the patient, the differential amplifier being coupled to the patient ground that is electrically isolated from earth ground by the isolation system, the capacitive coupling providing a low impedance path from an input of the differential amplifier for external noise that is within the bandwidth of the electrical signals being measured.

* * * * *